US010197486B2

(12) United States Patent
Mataei et al.

(10) Patent No.: US 10,197,486 B2
(45) Date of Patent: Feb. 5, 2019

(54) PAVEMENT DRAINAGE EVALUATION SYSTEM

(71) Applicants: Behrouz Mataei, Tehran (IR); Fereidoon Moghadas Nejad, Tehran (IR); Hamzeh Zakeri, Tehran (IR)

(72) Inventors: Behrouz Mataei, Tehran (IR); Fereidoon Moghadas Nejad, Tehran (IR); Hamzeh Zakeri, Tehran (IR)

(73) Assignees: Behrouz Mataei, Tehran (IR); Fereidoon Moghadas Nejad, Tehran (IR); Hamzeh Zakeri, Tehran (IR); Amirkabir University of Technology, Tehran (IR)

( * ) Notice: Subject to any disclaimer, the term of this patent is extended or adjusted under 35 U.S.C. 154(b) by 0 days.

(21) Appl. No.: 15/927,627

(22) Filed: Mar. 21, 2018

(65) Prior Publication Data
US 2018/0284004 A1 Oct. 4, 2018

Related U.S. Application Data

(60) Provisional application No. 62/492,200, filed on Apr. 30, 2017.

(51) Int. Cl.
*G01N 15/02* (2006.01)
*G06T 7/00* (2017.01)
(Continued)

(52) U.S. Cl.
CPC ..... *G01N 15/0227* (2013.01); *G01N 15/0211* (2013.01); *G01N 21/532* (2013.01);
(Continued)

(58) Field of Classification Search
CPC .......... G01N 15/0227; G01N 15/0211; G01N 21/532; G06T 7/0006
(Continued)

(56) References Cited

U.S. PATENT DOCUMENTS

| 4,690,553 | A | * | 9/1987 | Fukamizu | ............... G01W 1/14 250/341.8 |
| 5,218,206 | A | * | 6/1993 | Schmitt | ............... B60R 16/0237 250/339.1 |

(Continued)

FOREIGN PATENT DOCUMENTS

| CN | 104775349 B | 8/2016 |
| CN | 105780632 B | 8/2017 |

(Continued)

OTHER PUBLICATIONS

Wenting Luo, Surface drainage evaluation for rigid pavements using an inertial measurement unit and 1-mm three-dimensional texture data, Transportation Research Record: Journal of the Transportation Research Board 2457, 2014, pp. 121-128.

(Continued)

*Primary Examiner* — Roy M Punnoose
(74) *Attorney, Agent, or Firm* — NovoTechIP International PLLC

(57) ABSTRACT

A system for evaluating drainage condition of a pavement surface is disclosed. The system may include: a spray assembly configured to spray a liquid over the pavement surface, an image capturing device configured to capture consecutive images of the pavement surface at predetermined intervals, and an image processing unit coupled with the image capturing device. The image processing unit may include: a processor, and a memory that may be configured to store executable instructions to cause the processor to process the captured images to evaluate the drainage condition of the pavement by a number of steps that may include: converting each captured image into a binary image, the binary image including a first plurality of pixels representing pavement aggregates protruding from the sprayed liquid and a second plurality of pixels representing the sprayed liquid; applying optical granulometry to the (Continued)

binary images to obtain a rate of change for protruding pavement aggregates count and a rate of change for area of protruding pavement aggregates across the binary images; and classifying the pavement surface according to a drainage condition type based at least in part on a combination of the rate of change for the protruding pavement aggregates count and the rate of change for the area of protruding pavement aggregates.

20 Claims, 11 Drawing Sheets

(51) Int. Cl.
  *G01N 21/88* (2006.01)
  *G01N 21/53* (2006.01)
  *G01N 21/956* (2006.01)
(52) U.S. Cl.
  CPC ... *G01N 21/8851* (2013.01); *G01N 21/95607* (2013.01); *G06T 7/0006* (2013.01); *G01N 2021/8887* (2013.01); *G01N 2021/95615* (2013.01)
(58) Field of Classification Search
  USPC .......................................... 356/336
  See application file for complete search history.

(56) References Cited

U.S. PATENT DOCUMENTS

| | | | | |
|---|---|---|---|---|
| 5,521,594 A * | 5/1996 | Fukushima | ........ | B60G 17/0165 180/167 |
| 5,818,339 A * | 10/1998 | Giles | ...................... | G08B 19/02 340/583 |
| 6,765,353 B2 * | 7/2004 | Leleve | ................. | B60Q 1/0023 315/77 |
| 7,676,094 B2 * | 3/2010 | Hoki | ...................... | B60Q 1/085 382/104 |
| 8,248,256 B1 * | 8/2012 | Gerardi | ................... | G08B 21/20 340/604 |
| 8,796,627 B2 * | 8/2014 | Rockwell | ........... | G01N 21/4738 250/341.8 |
| 9,297,755 B2 * | 3/2016 | Renno | .................... | B64D 15/20 |
| 9,946,937 B2 * | 4/2018 | Faber | ...................... | G01W 1/00 |
| 2003/0103649 A1 * | 6/2003 | Shimakage | ........ | G06K 9/00798 382/104 |
| 2005/0047864 A1 * | 3/2005 | Yamada | .................. | G01W 1/14 404/71 |
| 2005/0167593 A1 * | 8/2005 | Forsyth | ................ | G01N 21/314 250/339.11 |
| 2011/0074955 A1 * | 3/2011 | Kuehnle | ................ | G01W 1/14 348/148 |
| 2012/0140233 A1 * | 6/2012 | Rockwell | ............... | G01N 21/55 356/445 |

FOREIGN PATENT DOCUMENTS

JP    2002250002 A    9/2002
KR    101508603 B1    4/2015

OTHER PUBLICATIONS

S. I. Sarsam, Field evaluation of Asphalt Concrete Pavement surface texture and skid characteristics, Proceedings, 5th Euroasphalt & Eurobitume Congress., 2012, pp. 13-15.

Behrouz Mataei, valuation of pavement surface drainage using an automated image acquisition and processing system, Automation in Construction, Dec. 6, 2017, vol. 86, pp. 240-255.

* cited by examiner

PAVEMENT DRAINAGE EVALUATION SYSTEM

CROSS-REFERENCE TO RELATED APPLICATION

This application claims the benefit of priority from pending U.S. Provisional Patent Application Ser. No. 62/492,200, filed on Apr. 30, 2017, and entitled "AUTOMATIC EVALUATION SYSTEM OF SURFACE DRAINAGE OF ASPHALT PAVEMENT," which is incorporated herein by reference in its entirety.

TECHNICAL FIELD

The present disclosure relates to pavement evaluation systems, particularly to systems and devices for evaluating drainage of a pavement surface.

BACKGROUND

Drainage condition of a pavement surface can affect road safety in wet conditions. For example, a poor drainage condition for a pavement surface can allow a layer or film of water to form on the surface, may result in hydroplaning or other conditions of reduced traction between the tires and the surface that may affect the steering, braking, or accelerating capabilities of the vehicle.

Factors that can bear on the drainage condition of a pavement can include, for example, pavement surface texture, surface rutting, pits, and signs drawn on the surface. The surface pavement texture may be considered as an important factor determining the drainage condition of the pavement surface. Technologies have been developed for evaluating pavement surface conditions, however, there is a need in the art for system and methods for evaluating drainage condition of a pavement. There is further a need in the art for an automated evaluation system for evaluating the drainage condition of the pavement surfaces.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a system for evaluating drainage condition of a pavement surface. The system may include: a spray assembly configured to spray a liquid over the pavement surface, an image capturing device configured to capture consecutive images of the pavement surface, and an image processing unit coupled with the image capturing device. In an aspect, intervals between the consecutive images can be predetermined. The image processing unit may include: a processor, and a memory that may be configured to store executable instructions to cause the processor to perform operations in a processing of the captured images to evaluate the drainage condition of the pavement by steps that may include: converting each captured image into a binary image, the binary image including a first plurality of pixels representing pavement aggregates protruding from the sprayed liquid and a second plurality of pixels representing the sprayed liquid; applying optical granulometry to the binary images to obtain a rate of change for protruding pavement aggregates count and a rate of change for area of protruding pavement aggregates across the binary images; and classifying the pavement surface according to a drainage condition type based at least in part on a combination of the rate of change for the protruding pavement aggregates count and the rate of change for the area of protruding pavement aggregates.

The above general aspect may include one or more of the following features. In one example, the liquid includes a colored liquid that may be colored such that a contrast may exist between the color of the pavement surface and the color of the colored liquid. According to one implementation, the system may further include a lighting assembly configured to project light to the pavement surface.

According to some implementations, the image capturing device may include: a camera that may be configured to capture a series of consecutive images from the pavement surface and a camera height adjustment mechanism coupled with the camera that may be configured to linearly move the camera along an axis perpendicular to the pavement surface. In another implementation, the system may further include an enclosure that may be configured to enclose the pavement surface from ambient light.

According to some implementations, the spray assembly may include nozzles, for example, two nozzles or more nozzles, and one or more of these may be positioned with predetermined angles and vertical distances from the pavement surface.

In another general aspect, the present disclosure describes a method for evaluating drainage condition of a pavement surface. The method may include one or more of the following steps: spraying a colored liquid over the pavement surface; capturing consecutive images of the target pavement surface; converting each captured image into a binary image, the binary image including a first plurality of pixels representing pavement aggregates protruding from the colored liquid and a second plurality of pixels representing the colored liquid; applying optical granulometry to consecutive binary images to obtain a rate of change for protruding pavement aggregates count and a rate of change for area of protruding pavement aggregates across the consecutive binary images; and classifying the pavement surface according to a drainage condition type based at least in part on a combination of the rate of change for the protruding pavement aggregates count and the rate of change for the area of protruding pavement aggregates.

According to some implementations, spraying a colored liquid over the pavement surface may include spraying a colored liquid with a color that has a contrast from the color of the target pavement surface. According to one implementation, converting each captured image into the binary image may include applying a thresholding method to each captured image.

According to some implementations, converting each captured image into a binary image may include converting each captured image into a binary image that can include a first plurality of pixels with a first intensity representing pavement aggregates protruding from the colored liquid and a second plurality of pixels with a second intensity representing the colored liquid. In an implementation, the first intensity can be assigned a first value, for example, logic 0, and the second intensity can be assigned a second value, for example, logic 1.

According to some implementations, applying optical granulometry to consecutive binary images may further include obtaining a rate of change for the protruding pavement aggregates surface distribution by dividing the rate of change for protruding pavement aggregates count by the rate of change for the area of protruding pavement aggregates by the predetermined interval.

According to some implementations, classifying the pavement surface according to a drainage condition type may include comparing the calculated rate of change for the protruding pavement aggregates surface distribution to a variation range for the rate of change for the protruding pavement aggregates surface distribution.

According to some implementations, classifying the pavement surface according to a drainage condition type may include comparing the calculated rate of change for protruding pavement aggregates count to a variation range for the rate of change for protruding pavement aggregates count.

According to some implementations, classifying the pavement surface according to a drainage condition type may include comparing the calculated rate of change for the area of protruding pavement aggregates to a variation range for the rate of change for the area of protruding pavement aggregates.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The following disclosure describes techniques and systems for evaluating drainage of a pavement surface. Disclosed systems and methods may include a drainage testing device that may be used to simulate the drainage process for a target pavement surface and capture consecutive images of the pavement surface during the drainage process. The disclosed systems and methods may further include an image processing unit that may process the captured images during the drainage process to evaluate surface drainage for the target pavement surface. As will be discussed below, such systems and methods may allow significant improvement and ease-of use in the evaluation process of a pavement surface by offering an automated evaluation system based on image processing.

Figure 1:
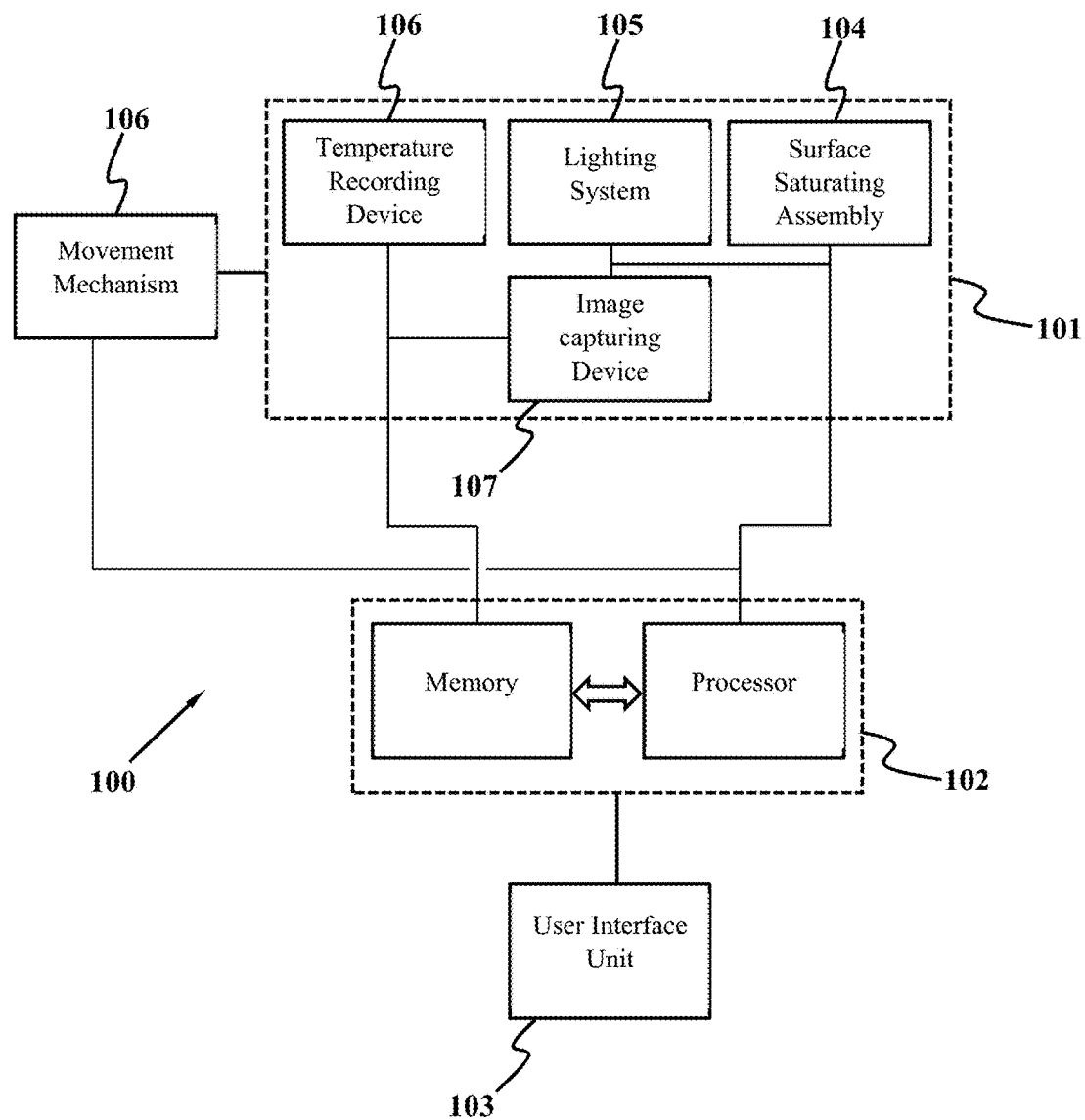
FIG. 1 is a schematic functional block diagram of one implementation of a pavement drainage evaluation system.

FIG. 1 is a schematic functional block diagram of one implementation of a pavement drainage evaluation system 100 according to one or more aspects. The pavement drainage evaluation system 100 may include a pavement drainage testing device 101, a processing unit 102, and optionally a user interface unit 103. The pavement drainage testing device 101 may simulate a drainage process on a target surface of a pavement in a controlled environment and then capture images of the target surface during the drainage process. In an implementation, the pavement drainage testing device 101 may include a surface saturating assembly 104, a lighting system 105, a temperature recording system 106, and an image capturing device 107.

Referring to FIG. 1, in an implementation, the surface saturating assembly 104 may be configured to spray a colored liquid onto the target surface of the pavement to cover the target surface with the colored liquid. According to one implementation, the colored liquid may be colored such that a contrast may exist between the pavement color and the color of the liquid. For example, in cases where the pavement is a black asphalt pavement, the colored liquid may be a white liquid.

Referring to FIG. 1, in an implementation, after the target surface is covered with the colored liquid, the image capturing device 107 may start capturing images of the target surface with specific intervals until the drainage process of the pavement surface is completed. In order to provide an appropriate illumination on the target surface, the lighting system 105 may project light toward the target surface from different angles.

According to some implementations, the target surface may be isolated from other environmental lights so that the lighting system 105 may function as the only light source for illuminating the target surface. This feature may provide a stable lighting condition for capturing images of the target surface independent of ambient light conditions.

Referring to FIG. 1, in an implementation, the processing unit 102 may be coupled to the pavement drainage testing device 101 and the user interface unit 103 through, for example, wired links (not explicitly visible in FIG. 1), wireless links (not explicitly visible in FIG. 1), or a combination of wired and wireless links. The processing unit 102 may be configured to process the captured images to evaluate surface drainage for the target pavement surface. The processing unit 102 may further be configured to control the surface saturating assembly 104, the lighting system 105, and the image capturing device 107 for purposes that may include, for example, adjusting the intervals between consecutive images and/or the height at which the image capturing device 107 captures the images of the target surface. Other controls the processing unit 102 can be configured to perform can include adjusting the amount of colored liquid sprayed over the target surface, and adjusting the light intensity and/or the height at which the lighting system 105 projects light toward the target surface.

With further reference to FIG. 1, in an implementation, the processing unit 102 may include a memory 108 and a processor 109. The memory 108 may include executable instructions that, when executed, cause the processor 109 to perform operations further to processes and methods disclosed herein. Such operations may include, for example, processing the received images from the image capturing device 107 to evaluate the surface drainage of the target surface. In an aspect, operations can include evaluating surface drainage based at least in part on determining a rate of drainage, and such determination can be performed, for example, by calculations that can compare consecutively captured images of the target surface during the drainage process Referring to FIG. 1, in an implementation, the user interface unit 103 may be configured to display the evaluation results of the surface drainage of the target surface. According to an implementation, the user interface unit 103 may include a graphical user interface unit (GUI) that may be optionally configured to receive data input from a user. Data input by the user may include, for example, a desirable interval for capturing the consecutive images by the image capturing device 107 or commands regarding the height of the image capturing device 107 or the height of the lighting system 105 from the target surface.

With reference to FIG. 1, in some implementations, the pavement drainage evaluation system 100 may also be coupled with a movement mechanism 110. The movement mechanism 110 may include an actuator (not explicitly visible in FIG. 1) that may be coupled to the processor 109. The user interface unit 103, in combination with the processor 109, may allow a user to interactively control the movements of the pavement drainage evaluation system 100. According to some implementations, the user may input movement commands via a controller (not explicitly visible in FIG. 1). The controller may be coupled to the user interface unit 103 through, for example, wired links, wireless links, or a combination of wired and wireless links. The movement mechanism 110 may provide mobility to the pavement drainage evaluation system 100, for example, a capability of moving the pavement drainage evaluation system 100 over the pavement surface to evaluate different portions of, for example, a road pavement.

Figure 2A:
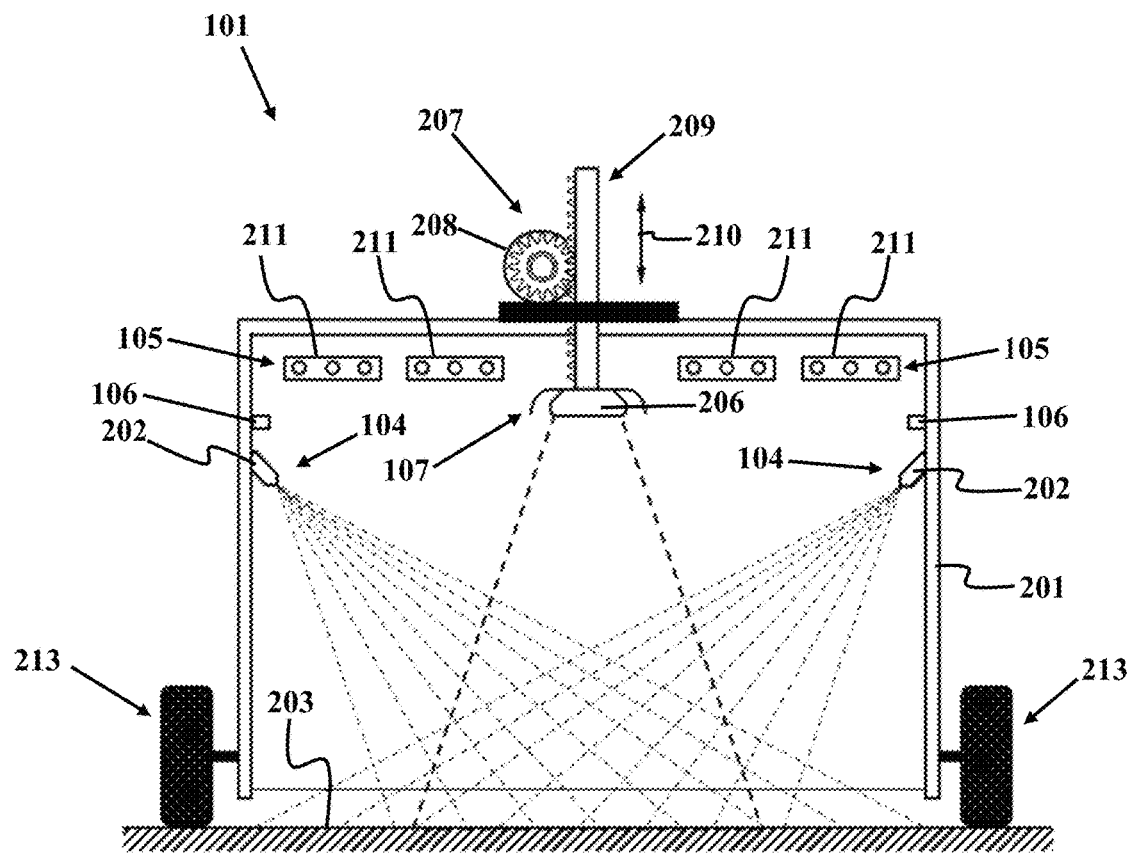
FIG. 2A shows a schematic representation of one implementation of the drainage testing device.
Figure 2B:
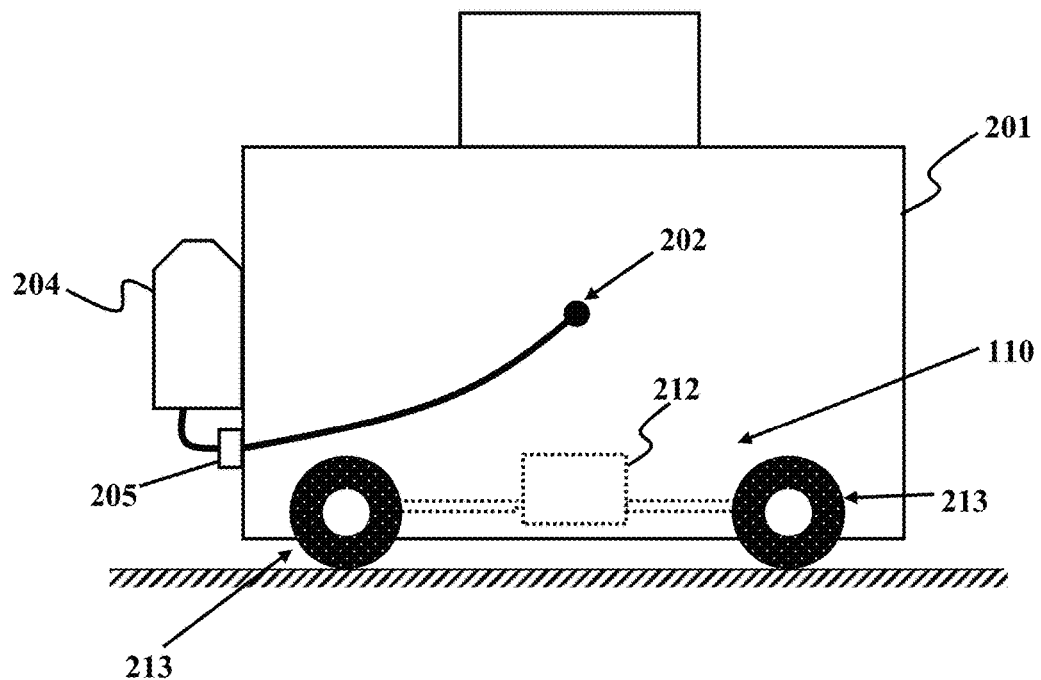
FIG. 2B shows a schematic side-view representation of one implementation of the drainage testing device.

FIG. 2A shows a schematic representation of one implementation of the drainage testing device 101 and FIG. 2B shows a schematic side-view representation of one implementation of the drainage testing device 101. Referring to FIG. 2A, the drainage testing device 101 may include an enclosure 201 that may isolate the pavement drainage testing environment from the surrounding environment. According to some implementations, the surface saturating assembly 104, the lighting system 105, the temperature recording system 106, and the image capturing device 107 may be enclosed inside the enclosure 201.

Referring to FIGS. 2A and 2B, in an implementation, the surface saturating assembly 104 may include, for example, two or more nozzles 202 that may be installed at either sides of the inner section of the enclosure 201. The nozzles 202 may be positioned with predetermined angles and vertical distances from a target surface 203 to ensure a complete coverage of the target surface 203 by the liquid jets that are sprayed from these nozzles 202 onto the target surface 203. For purposes of description, the target surface 203 can be the portion of the pavement immediately bellow the enclosure 201.

According to some implementations, the surface saturating assembly 104 may further include a liquid reservoir 204 for storing the colored liquid, and a pumping device 205 for pumping the colored liquids via the nozzles 202 onto the target surface 203. The liquid reservoir 204, the pumping device 205, and the nozzles 202 may be in fluid communication via a plurality of conduits, e.g., tubes or pipes (not explicitly labeled in FIGS. 2A and 2B).

Referring to FIG. 2A, in an implementation, the image capturing device 107 may include a camera 206 and a camera height adjustment mechanism 207. The camera 206 may be positioned above the target surface 203 with a predetermined vertical distance from the target surface 203. The camera 206 may capture a series of consecutive images from the target surface 203 with predetermined intervals during the pavement drainage process. It will be understood that "consecutive images" are not necessarily concatenated in time. For example, images can be captured at each time increment in a succession of time increments, and every Nth image, e.g., every third, or every other, image can be used, whereupon the Nth images may be "consecutive images." In another implementation, the camera 206 can be configured to apply a time stamp to images, and the difference between time stamps can be used in calculating the various rates, as described in greater detail in later sections of this disclosure.

According to some implementations, the camera 206 may be coupled with a camera height adjustment mechanism 207. The camera height adjustment mechanism 207 may include a motor 208 coupled with the camera 206, for example, via a linear actuator 209. The linear actuator 209 may be, for example, a rack and pinion mechanism and may be configured to linearly move the camera 206 along axis 210 that is substantially perpendicular to the target surface 203.

Referring to FIG. 2A, in an implementation, the lighting system 105 may include a light source 211, or plurality of light sources 211, such as a number of LEDs that may be arranged around an upper portion of the enclosure 201. The light sources 211 may provide the required light for capturing relatively high quality images from the target surface 203. The enclosure 201 in combination with the light sources 211 allow the drainage testing device 101 to simulate the drainage process regardless of the environmental conditions and ambient light. For example, the enclosure 201 in combination with the light sources 211 can enable evaluation processes as disclosed herein to be carried out at night.

With reference to FIG. 2A, in an implementation, the temperature recording system 106 may include one or more thermometers, e.g., four thermometers that may be arranged, for example, at four sides of the enclosure 201 to record the temperature during the drainage evaluation process. It will be understood that the above example quantity and arrangement of thermometers is only for purposes of illustration, and is not intended to limit the scope of the disclosed methods or systems. The recorded temperature may, for example, be later used to take into account the effect of temperature of the drainage quality of the target surface 203.

Referring to FIGS. 2A and 2B, in an implementation, the movement mechanism 110 may include a main motor 212 that may be coupled to a plurality, for example, four tires 213. With further reference to FIG. 1, the main motor 212 may be coupled to the processor 109 and the processor 109, in combination with the user interface unit 103, may allow the user to control the movement of the drainage testing device 101 over the pavement.

Figure 3:
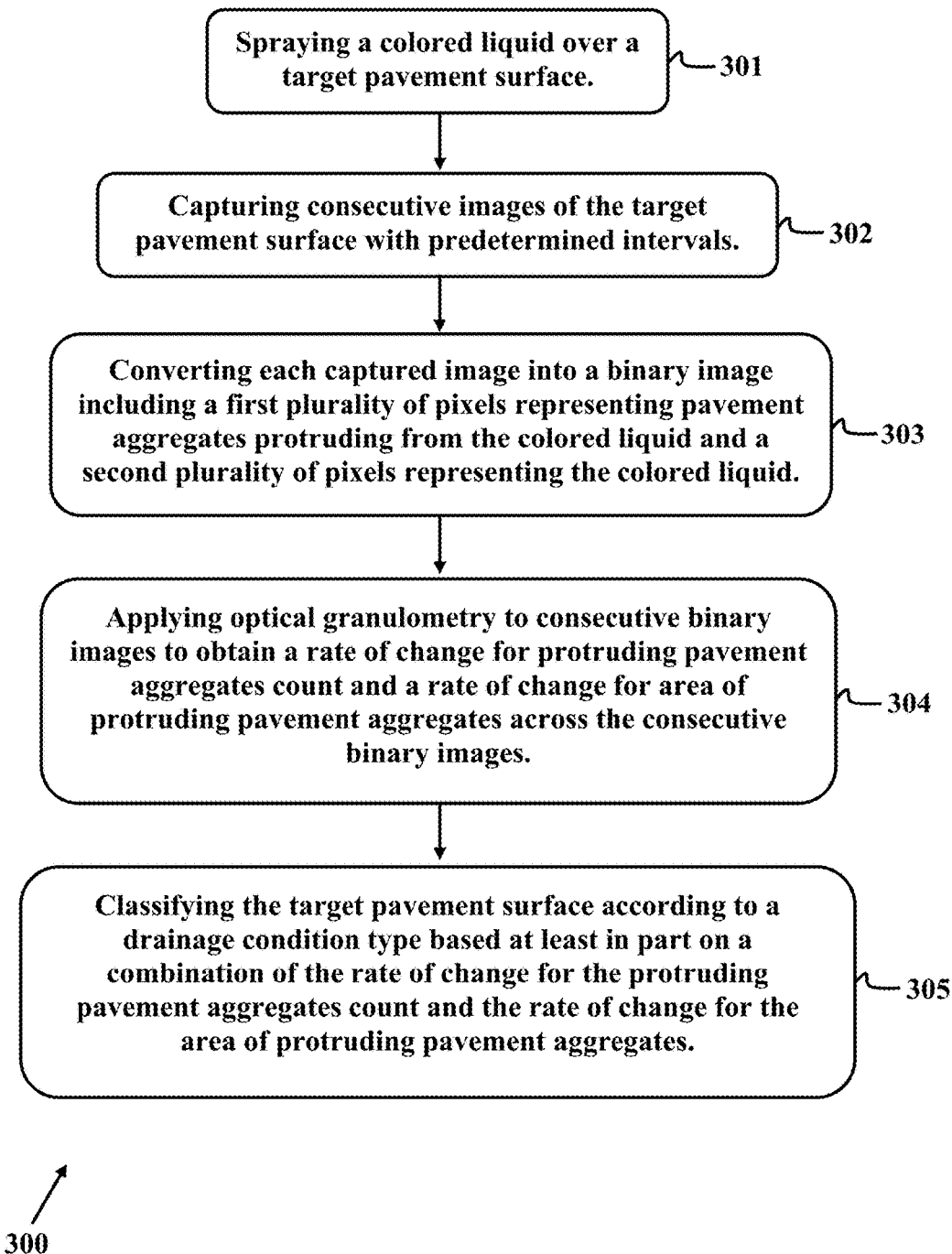
FIG. 3 is a logic flow chart illustrating operations in a method for evaluating drainage of a pavement surface according to one or more implementations of the present disclosure.

FIG. 3 illustrates a method 300 for evaluating drainage condition of a target pavement surface according to one or more implementations of the present disclosure. In one implementation, the method 300 may include a step 301 of spraying a colored liquid over the target pavement surface; a step 302 of capturing consecutive images of the target pavement surface with predetermined intervals; a step 303 of converting each captured image into a binary image including a first plurality of pixels representing pavement aggregates protruding from the colored liquid and a second plurality of pixels representing the colored liquid; a step 304 of applying optical granulometry to consecutive binary images to obtain a rate of change for protruding pavement aggregates count and a rate of change for area of protruding pavement aggregates across the consecutive binary images; and a step 305 of classifying the target pavement surface according to a drainage condition type based at least in part on a combination of the rate of change for the protruding pavement aggregates count and the rate of change for the area of protruding pavement aggregates. It will be understood that the rate of change can be based, e.g., scaled, at least in part, according to the predetermined intervals. In one exemplary operation, the step 302 captured consecutive images can include a captured first image and a captured second image, and respective capture times of the captured first image and the captured first image can be spaced apart by a time difference, e.g., the predetermined interval. In this exemplary operation, step 303 converting each of the captured consecutive image into a binary image can include converting the captured first image into a first binary image and converting the captured second image into a second binary image. In the example, step 304 processing can include applying optical granulometry to the first binary image and second binary image, as described in greater in later sections of this disclosure. In this example, the rate of change for protruding pavement aggregates count and the rate of change for area of protruding pavement aggregates across the binary images can be based, at least in part, on the time difference.

Additional details regarding these steps are provided below.

With respect to the step 301, in some implementations, spraying a colored liquid over the target pavement surface may include spraying a colored liquid with a color that has a contrast from the color of the target pavement surface. For example, in cases where the target pavement surface is a dark-colored asphalt pavement, the colored liquid may be a white liquid. According to some implementation, different color pigments may be mixed in with a suitable liquid such as water to obtain the colored liquid and the color pigment may be chosen based on the color of the target pavement surface such that a contrast may exist between the target pavement color and the color of the liquid. In one implementation, spraying the colored liquid over the target pavement surface may include spraying the colored liquid over the target surface until the target pavement surface is saturated with the colored liquid.

With further reference to FIGS. 2A and 2B, in an implementation, step 301 may be carried out by the surface saturating assembly 104 of the pavement drainage testing device 101, where the colored liquid may be stored in the liquid reservoir 204 and it may be sprayed over the target surface 203 via the nozzles 202 of the surface saturating assembly 104.

With respect to the step 302, according to some implementations, once the target pavement surface is covered with the colored liquid, consecutive images of the target surface may be captured with predetermined intervals to record the drainage process of the colored liquid from the target surface. At the beginning of the drainage process only a few aggregates of the target pavement surface protrude from the colored liquid. As the drainage process goes on, more aggregates protrude from the colored liquid. In one implementation, the predetermined interval may be selected such that different stages of the drainage process may be captured in the consecutive images taken from the target surface.

With further reference to FIGS. 2A and 2B, in an implementation, step 302 may be carried out by the pavement drainage testing device 101, where the target pavement surface 203 may be illuminated by the lighting system 105 and consecutive images may be captured from the target pavement surface by the camera 206 of the image capturing device 107.

Figure 4:
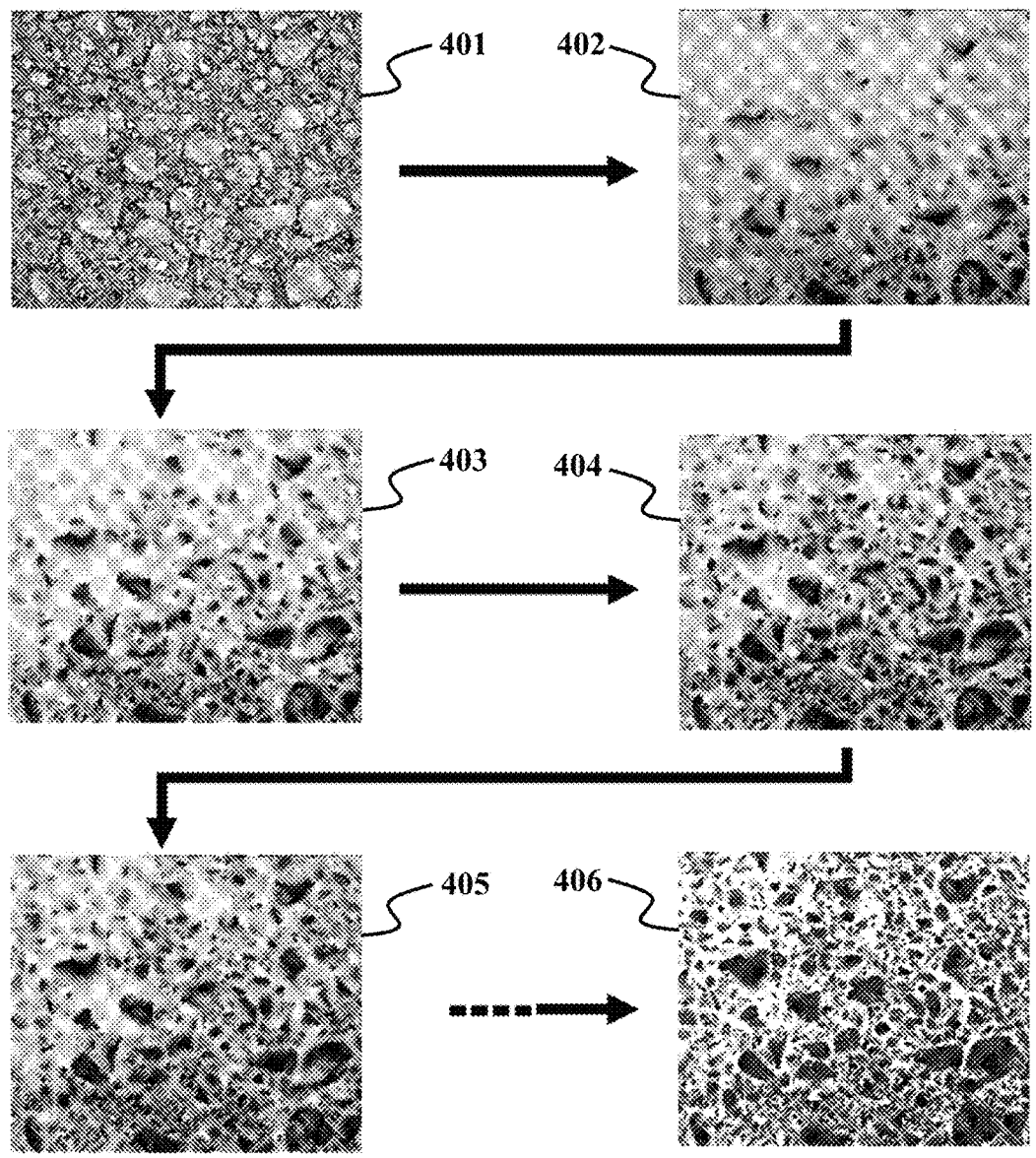
FIG. 4 depicts consecutive images captured from a target surface during the pavement drainage testing process, according to one implementation of the present disclosure.

FIG. 4 depicts consecutive images 401 to 406 captured from an exemplary target surface during the pavement drainage testing process, according to one implementation of the present disclosure. Referring to FIG. 4, image 401 is an image captured from the dry target surface. The dry target surface is then sprayed with a colored liquid, a white liquid in this example. Image 402 is an image captured from the target surface saturated by the sprayed white liquid. In image 402 aggregates of the target surface are visible as darker spots. From this point on, the drainage of the white liquid starts and as the drainage process goes on more aggregates protrude from the surface of the white liquid. This can be seen in consecutive images 403, 404, 405 where more aggregates protrude from the surface of the white liquid as time passes. Images 402 to 405 are captured by for example 2-minute intervals. Image 406 is an image that is captured from the target surface at the end of the drainage process. As can be seen in image 406, the white liquid is mostly drained and more protruding aggregates are visible.

According to some implementations, the step 303 may involve converting each captured image into a binary image including a first plurality of pixels representing pavement aggregates protruding from the colored liquid and a second plurality of pixels representing the colored liquid. The first plurality of pixels may have a first intensity and the second plurality of pixels may have a second intensity. In one implementation, an image segmentation method, such as thresholding may be applied to each captured image to create the binary image of each captured image. The contrast between the color of the sprayed liquid and the color of the pavement aggregates protruding from the sprayed liquid may create a difference between the intensity of the pixels representing the sprayed liquid and the pixels representing the aggregates. A predetermined threshold may be selected and the pixels with intensities lower than that threshold may be replaced with pixels that have the first intensity and represent the aggregates, and the pixels with intensities higher than that threshold may be replace with pixels that have the second intensity and represent the sprayed liquid.

Furthermore, in some implementations, some preprocessing steps may optionally be carried out before step 303 of converting each captured image into the binary image. There may exist numerous types of noise and artifacts in the captured images from the target pavement surface that may degrade the quality of the captured images. The low quality of the captured images may affect the accuracy of image processing techniques, such as thresholding and edge detection that are to be applied to the captured images. According to some implementations, the preprocessing steps may include a denoising step where image noise is removed from the captured images while important signal features of the captured images are retained as much as possible. The preprocessing steps may further include an image compression step where the volume of data needed for representing each captured image is reduced. Different methods and techniques may be used for denoising and compressing the captured images, such as, but not limited to, wavelet transform, ridgelet transform, curvelet transform, shearlet transform, and contourlet transform.

Referring to FIG. 3, in some implementations, step 304 may involve applying optical granulometry to the consecutive binary images. The optical granulometry may include edge detection of the target surface aggregates in the captured images. First the edges of the target surface aggregates are detected and then target surface aggregates may be counted and stored as protruding pavement aggregates count; and the surface area of target surface aggregates may be measured and stored as the area of protruding pavement aggregates.

According to some implementations, a rate of change for protruding aggregates count may be calculated by dividing a sum of protruding aggregates count in each captured image by the predetermined time interval by which the images are captured. Equation (1) below may be used to calculate the rate of change for protruding aggregates count:

$$Q_N = \frac{\sum_i^n N_i}{t} \quad \text{Equation (1)}$$

In Equation (1) above, $Q_N$ represents the rate of change for protruding aggregates count across the consecutive images taken from the drainage process; $N_i$ represents protruding pavement aggregates count in i-th image; n is the total number of consecutive images; and $\Delta t$ is the predetermined time interval by which the images are captured.

According to some implementations, a rate of change for the area of protruding pavement aggregates may be calculated by dividing a sum of the area of protruding pavement aggregates in each captured image by the predetermined time interval by which the images are captured. Equation (2) below may be used to calculate the rate of change for the area of protruding pavement aggregates:

$$Q_A = \frac{\sum_i^n A_i}{t} \quad \text{Equation (2)}$$

In Equation (2) above, $Q_A$ represents the rate of change for the area of protruding pavement aggregates across the consecutive images taken from the drainage process; $A_i$ represents the area of protruding pavement aggregates in i-th image; n is the total number of consecutive images; and $\Delta t$ is the predetermined time interval by which the images are captured.

According to some implementations, an index may be defined as protruding pavement aggregates surface distribution. A rate of change for the protruding pavement aggregates surface distribution may be calculated by Equation (3) below:

$$Q_P = \frac{(\sum_i^n N_i)/(\sum_i^n A_i)}{t} \quad \text{Equation (3)}$$

In Equation (3) above, $Q_P$ represents the rate of change for the protruding pavement aggregates surface distribution across the consecutive images taken from the drainage process; $N_i$ represents protruding pavement aggregates count in i-th image; $A_i$ represents the area of protruding pavement aggregates in i-th image; n is the total number of consecutive images; and $\Delta t$ is the predetermined time interval by which the images are captured.

Figure 5A:
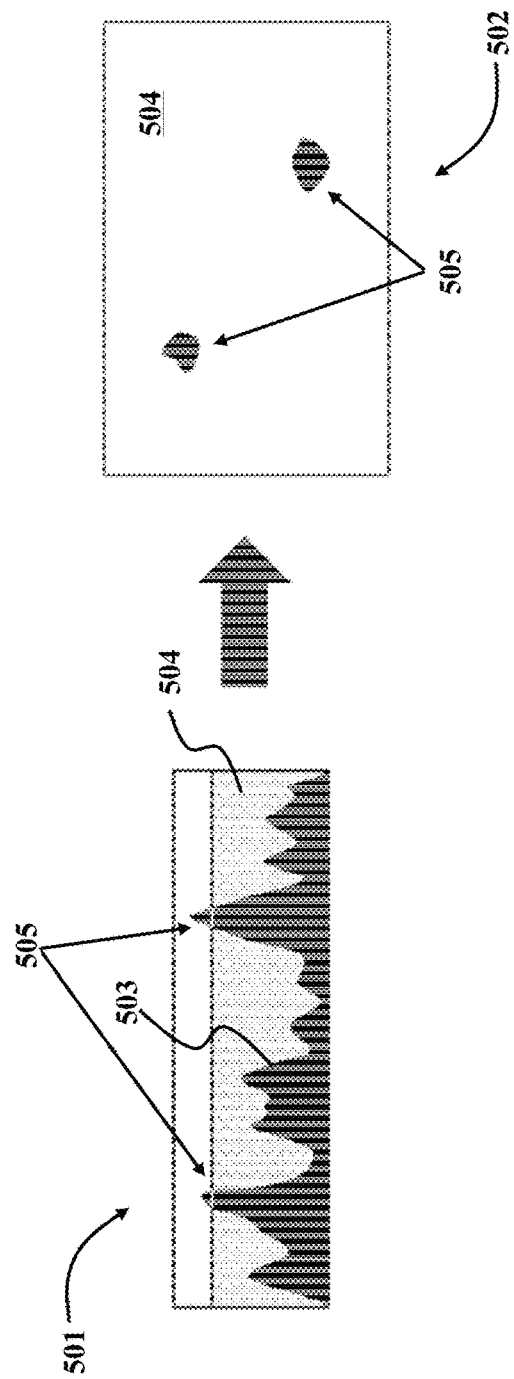
FIG. 5A illustrates a simplified schematic representation of a side-view of an exemplary drainage process and binary images obtained for the exemplary drainage process.

FIG. 5A illustrates a simplified schematic representation of a side-view 501 of an exemplary pavement drainage process and a corresponding binary image 502 obtained for the exemplary drainage process. Referring to FIG. 5A, in the side-view 501, pavement aggregates 503 and sprayed liquid 504 over the target surface are visible. As can be seen in the side-view 501, some pavement aggregates 503 are protruding from the surface of the sprayed liquid 504. In the corresponding binary image 502 which is obtained by capturing an image from above the target surface and then thresholding the captured image, the protruding aggregates 505 appear as spots with a first intensity and the sprayed liquid 504 appears as surrounding pixels with a second intensity. For example, in the binary image 502, protruding aggregates 505 appear as dark spots with the first intensity of 0 and the sprayed liquid 504 appears as white surrounding pixels with the second intensity of 1. With further reference to step 304 of FIG. 3, optical granulometry may be applied to the binary image 502 an thereby detecting the edges of the protruding aggregates 505. Once the edges of the protruding aggregates 505 is detected then the protruding aggregates 505 may be counted to obtain the protruding aggregates count for the binary image 502. In this example, the protruding aggregates count for the binary image 502 is equal to 2. The area of the protruding aggregates 505 may simply be calculated by for example counting the pixels with the first intensity.

Figure 5B:
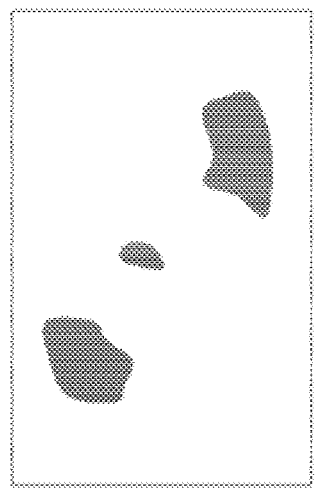
FIGS. 5B to 5D illustrate simplified schematic representations of side-views of the FIG. 5A schematically represented exemplary pavement drainage process and corresponding binary images, according to one implementation of the present disclosure.
Figure 5B:
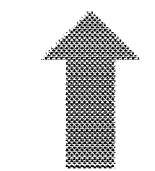
Figure 5B:
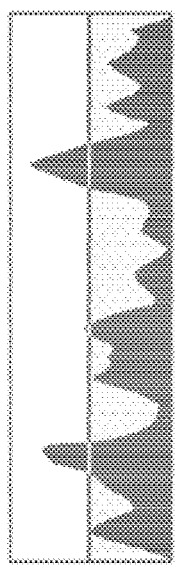
Figure 5C:
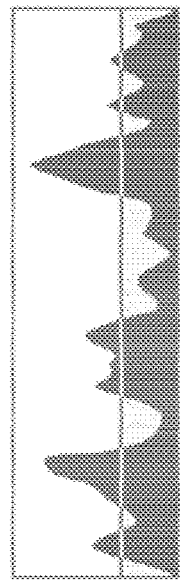
Figure 5C:
Figure 5C:
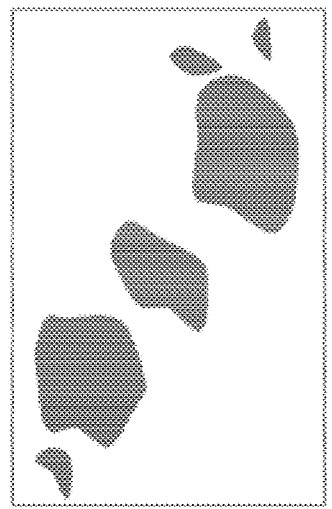
Figure 5D:
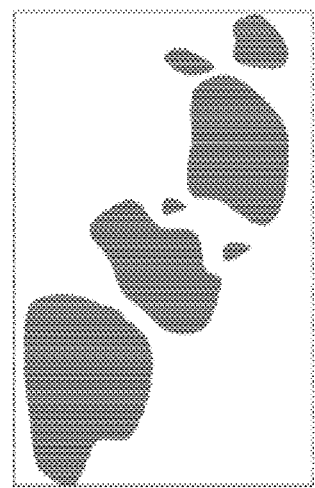
Figure 5D:
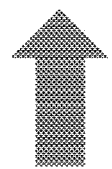
Figure 5D:
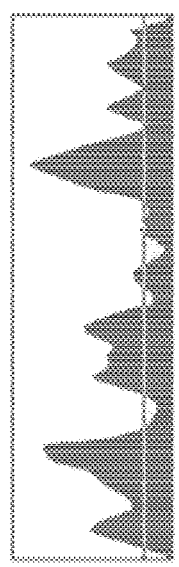

FIGS. 5B to 5D illustrate simplified schematic representations of side-views of the exemplary pavement drainage process and corresponding binary images as the exemplary drainage process goes on. Referring to FIGS. 5B to 5D, as the drainage process continues, more aggregates protrude from the surface of the sprayed liquid and, as a result, the protruding aggregates count and the area of the protruding aggregates change with time. Based on the protruding aggregates count and the area of the protruding aggregates obtained for each captured image and the predetermined interval between the captured images, the rate of change for protruding aggregates count, the rate of change for the area of protruding pavement aggregates, and the rate of change for the protruding pavement aggregates surface distribution may be calculated, for example, as described in the preceding sections of the present disclosure.

Referring back to FIG. 3, once the rate of change for the protruding aggregates count and the rate of change for the area of protruding aggregates are obtained in step 304, the method 300 may proceed to the step 305 of classifying the target pavement surface according to a drainage condition type based at least in part on a combination of the the rate of change for the protruding aggregates count and the rate of change for the area of protruding aggregates. To this end, in one implementation, the rate of change for protruding aggregates count calculated by Equation (1), the rate of change for the area of protruding aggregates calculated by Equation (2), and the rate of change for the protruding pavement aggregates surface distribution calculated by Equation (3) may be used to evaluate the rate of drainage for the target pavement surface.

Figure 6:
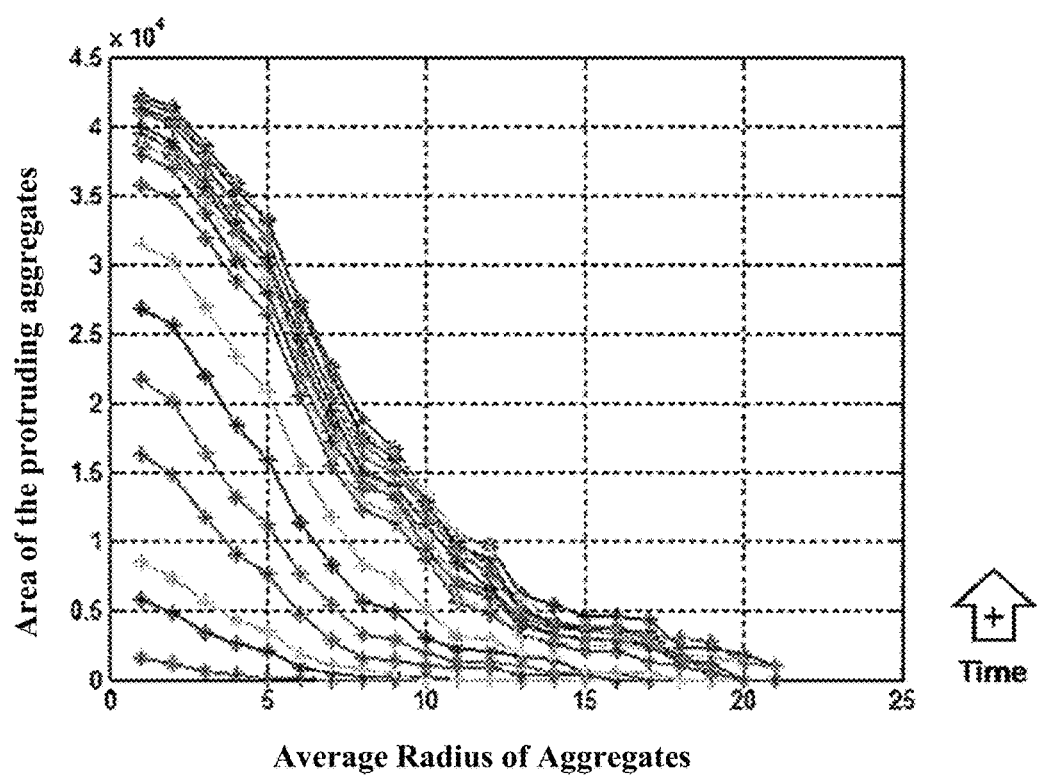
FIG. 6 illustrates an exemplary granulometry diagram obtained for an exemplary pavement.

FIG. 6 illustrates an exemplary granulometry diagram 600 obtained for an exemplary pavement by performing steps 301 to 304 of method 300 of FIG. 3. The exemplary granulometry diagram 600 is a diagram of area of the protruding aggregates versus average radius of aggregates obtained from the optical granulometry for each captured image. Each data series in this diagram corresponds to a captured image in a certain time during the drainage process. As the time passes the series shift upwardly, therefore the lower series belong to earlier stages of the drainage and the upper series relate to the later stages of the drainage process. Referring to the granulometry diagram 600, as the drainage process goes on, the area of the protruding aggregates increases. The rate of this increase in the area of the protruding aggregates is higher at earlier stages of the drainage process and then this rate decreases as time passes. According to some implementation, by obtaining granulometry diagrams similar to the granulometry diagram 600 for a plurality of different pavements, variation ranges may be obtained for the rate of change for protruding aggregates count ($Q_N$), the rate of change for the area of protruding aggregates ($Q_A$), and the rate of change for the protruding pavement aggregates surface distribution ($Q_P$) for three drainage condition types of good, normal, and bad.

Referring back to FIG. 3, with respect to step 305, in one implementation, classifying the target pavement surface according to a drainage condition type based at least in part on a combination of the the rate of change for the protruding aggregates count and the rate of change for the area of protruding aggregates may include comparing the calculated rates of change for the following three rates of change: the rate of change for protruding aggregates count ($Q_N$), the rate of change for the area of protruding aggregates ($Q_A$) and the rate of change for the protruding pavement aggregates surface distribution ($Q_P$) to the variation ranges obtained for $Q_N$, $Q_A$, $Q_P$ corresponding to the drainage condition type.

Referring to FIG. 1, according to one implementation, the memory 108 may include executable instructions that, when executed, cause the processor 109 to perform operations further to method 300 of FIG. 3. The processor 109 may convert each captured image to a binary image, apply optical granulometry to the binary images to obtain or otherwise calculate the rate of change for protruding aggregates count ($Q_N$), the rate of change for the area of protruding aggregates ($Q_A$), and the rate of change for the protruding pavement aggregates surface distribution ($Q_P$). The user interface unit 103 may be configured to display the calculated $Q_N$, $Q_A$, and $Q_P$ and a user may classify the target pavement surface according to a drainage condition type based on the calculated $Q_N$, $Q_A$, and $Q_P$.

The memory 108 may further include standard ranges obtained for the rate of change for protruding aggregates count ($Q_N$), the rate of change for the area of protruding aggregates ($Q_A$), and the rate of change for the protruding pavement aggregates surface distribution ($Q_P$). The processor 109 may convert each captured image to a binary image, apply optical granulometry to the binary images to obtain or otherwise calculate the rate of change for protruding aggregates count ($Q_N$), the rate of change for the area of protruding aggregates ($Q_A$), and the rate of change for the protruding pavement aggregates surface distribution ($Q_P$), and then compare the calculated $Q_N$, $Q_A$, and $Q_P$, with their respective variation ranges in order to classify the target pavement surface according to a drainage condition type. The drainage condition types may include, for example, good, normal, and bad. It will be understood that "good," "normal," and "bad" are only examples of names that can be assigned to drainage condition types, and are not intended as an any limitation on the scope of names that can be assigned to drainage condition types. For example, letter designations, e.g., "A," "B," "C," and so forth, can be used. It will also be understood that three drainage condition types is only one example quantity of types, and that other quantities, e.g., two, or four or more can be used.

EXAMPLE

Figure 7:
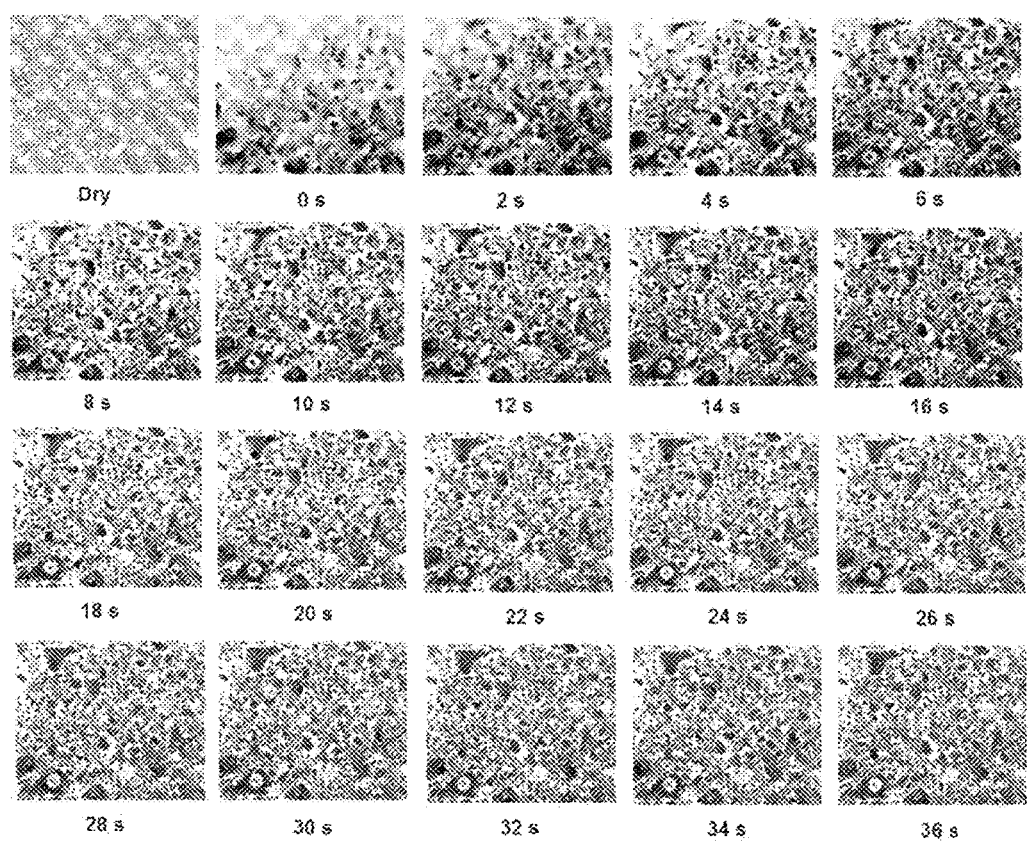
FIG. 7 illustrates captured images of a first example asphalt pavement surface with predetermined intervals of 2 seconds, according to one implementation of the present disclosure.

FIG. 7 illustrates captured images of the first example asphalt pavement surface with predetermined intervals of 2 seconds. Theses captured images are then processed to obtain $Q_N$, $Q_A$, and $Q_P$ for each time interval. Table 1 reports the obtained $Q_N$, $Q_A$, and $Q_P$ for the first example asphalt pavement surface.

TABLE 1

|  | Time (s) | | | | | | | |
| --- | --- | --- | --- | --- | --- | --- | --- | --- |
|  | 2 | 4 | 6 | 8 | 10 | 12 | 14 | 16 |
| $Q_N$ | 49.5 | 13.2 | 44.5 | 57.5 | −5.5 | −3.5 | −13.5 | 34 |
| $Q_A$ | 1469 | 2682 | 2768 | 769 | 1974 | 1639 | 1217 | 290 |
| $Q_P * 10^{-4}$ | 169 | 246 | 80 | 373 | −14 | −11 | −55 | 586 |

|  | Time (s) | | | | | | |
| --- | --- | --- | --- | --- | --- | --- | --- |
|  | 18 | 20 | 22 | 24 | 26 | 28 | 30 |
| $Q_N$ | −19 | −30 | −4 | −16.5 | 11.5 | −29 | −4 |
| $Q_A$ | 955 | 502 | 680 | 514 | 163 | 664 | 185 |
| $Q_P * 10^{-4}$ | −99 | −298 | −29 | −161 | 353 | −218 | −108 |

Referring to Table 1, $Q_N$ has higher values within the first few seconds of the pavement drainage process and then it decreases. A similar trend may be observed for $Q_A$. Higher values of $Q_N$ and $Q_A$ in the first few seconds of the drainage process may be interpreted as a higher drainage rate in the first few seconds of the drainage process. Negative values for $Q_N$ means a decrease in the protruding aggregate count. This phenomenon is due to the drop in the sprayed liquid level, where small aggregates join together to form a larger aggregate. As a result, the protruding aggregate count decreases while the area of protruding aggregates increases.

According to some implementation, by obtaining granulometry diagrams for a plurality of different pavements, and calculating $Q_N$, $Q_A$, and $Q_P$ for the plurality of pavements, variation ranges may be obtained for $Q_N$, $Q_A$, and $Q_P$ for three drainage condition types of good, normal, and bad. According to one implementation, for a good drainage condition, average $Q_N$ is greater than 25, average $Q_A$ is greater than 1000, and $Q_P$ is between 0.015 and 0.02. According to one implementation, for a normal drainage condition, average $Q_N$ is greater than 21, average $Q_A$ is greater than 900, and $Q_P$ is between 0.013 and 0.018. According to one implementation, for a bad drainage condition, average $Q_N$ is less than 21, average $Q_A$ is less than 900, and $Q_P$ is less than 0.013.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for evaluating drainage condition of a pavement surface, the system comprising:
   a spray assembly configured to spray a liquid over the pavement surface;
   an image capturing device configured to capture consecutive images of the pavement surface; and
   an image processing unit coupled with the image capturing device, the image processing unit including:
      a processor; and
      a memory configured to store executable instructions to cause the processor to process the captured consecutive images to evaluate the drainage condition of the pavement surface, the operations including:
         converting each of the captured consecutive images into a binary image, the binary image including a first plurality of pixels representing pavement aggregates protruding from the sprayed liquid and a second plurality of pixels representing the sprayed liquid;
         applying optical granulometry to the binary images to obtain a rate of change for protruding pavement aggregates count and a rate of change for area of protruding pavement aggregates across the binary images; and
         identifying the drainage condition, from among a given plurality of drainage conditions, based at least in part on a combination of the rate of change for the protruding pavement aggregates count and the rate of change for the area of protruding pavement aggregates.

2. The system of claim 1, wherein:
the given plurality of drainage conditions includes a given plurality of drainage condition types,
the given plurality of drainage condition types includes a good drainage condition and a bad drainage condition, and
identifying the drainage condition includes classifying the drainage condition into a drainage condition types among the given plurality of drainage condition types.

3. The system of claim 1, wherein:
the image capturing device is configured to capture consecutive images of the pavement surface at predetermined intervals, and
applying optical granulometry to the binary images is configured wherein the rate of change for protruding pavement aggregates count and the rate of change for area of protruding pavement are each based, at least in part, on the predetermined intervals.

4. The system of claim 1, wherein:
captured consecutive images include a captured first image and a captured second image, wherein respective capture times of the captured first image and the captured first image are spaced apart by a time difference,
converting each of the captured consecutive image into a binary image includes converting the captured first image into a first binary image and converting the captured second image into a second binary image, and
applying optical granulometry to the binary images is configured wherein the rate of change for protruding pavement aggregates count and the rate of change for area of protruding pavement aggregates across the binary images are each based, at least in part, on the time difference.

5. The system according to claim 1, wherein the liquid includes a colored liquid, the colored liquid being of a color such that a contrast exists between a color of the pavement surface and the color of the colored liquid.

6. The system according to claim 1, further comprising a lighting assembly, the lighting assembly being configured to project light toward the pavement surface.

7. The system according to claim 1, wherein the image capturing device includes:
a camera, the camera being configured to capture a series of the consecutive images from the pavement surface at predetermined intervals; and
a camera height adjustment mechanism coupled with the camera configured to linearly move the camera along an axis perpendicular to the pavement surface.

8. The system according to claim 1, further comprising an enclosure configured to enclose the pavement surface from ambient light.

9. The system according to claim 1, wherein the spray assembly includes at least two nozzles, and at least one of the at least two nozzles is positioned with a predetermined angle relative to the pavement surface.

10. A method for evaluating drainage condition of a pavement surface, the method comprising:
spraying a liquid over a target pavement surface;
capturing consecutive images of the target pavement surface;
converting each captured image into a binary image, the binary image including a first plurality of pixels representing pavement aggregates protruding from the colored liquid and a second plurality of pixels representing the colored liquid;
applying optical granulometry to consecutive binary images to obtain a rate of change for protruding pavement aggregates count and a rate of change for area of protruding pavement aggregates across the consecutive binary images; and
identifying the drainage condition of the pavement surface, from among a given plurality of drainage conditions, based at least in part on a combination of the rate of change for the protruding pavement aggregates count and the rate of change for the area of protruding pavement aggregates.

11. The method of claim 10, wherein:
capturing consecutive images of the pavement surface includes capturing consecutive images of the pavement surface at predetermined intervals, and
applying optical granulometry to the binary images is configured wherein the rate of change for protruding pavement aggregates count and the rate of change for area of protruding pavement are each based, at least in part, on the predetermined intervals.

12. The method of claim 10, wherein:
capturing consecutive images include capturing a first image and capturing second image, wherein respective capture times of the captured first image and the captured first image are spaced apart by a time difference,
converting each of the captured consecutive image into a binary image includes converting the captured first image into a first binary image and converting the captured second image into a second binary image, and
applying optical granulometry to the binary images is configured wherein the rate of change for protruding pavement aggregates count and the rate of change for area of protruding pavement aggregates across the binary images are each based, at least in part, on the time difference.

13. The method according to claim 10, wherein spraying a colored liquid over the pavement surface includes spraying a colored liquid with a color that has a contrast from the color of the target pavement surface.

14. The method according to claim 10, wherein converting each captured image into the binary image includes applying a thresholding method to each captured image.

15. The method according to claim 10, wherein converting each captured image into a binary image includes converting each captured image into a binary image, the binary image including a first plurality of pixels with a first intensity of zero representing pavement aggregates protruding from the colored liquid and a second plurality of pixels with a second intensity of 1 representing the colored liquid.

16. The method according to claim 10, wherein applying optical granulometry to consecutive binary images further includes obtaining a rate of change for the protruding pavement aggregates surface distribution by dividing the rate of change for protruding pavement aggregates count by the rate of change for the area of protruding pavement aggregates by the predetermined interval.

17. The method of claim 16, wherein:
the given plurality of drainage conditions includes a given plurality of drainage condition types,
the given plurality of drainage condition types includes a good drainage condition and a bad drainage condition, and
identifying the drainage condition includes classifying the drainage condition into a drainage condition types among the given plurality of drainage condition types.

18. The method according to claim 17, wherein classifying the pavement surface according to a drainage condition type includes comparing the calculated rate of change for the protruding pavement aggregates surface distribution to a variation range for the rate of change for the protruding pavement aggregates surface distribution.

19. The method according to claim 17, wherein classifying the pavement surface according to a drainage condition type includes comparing the calculated rate of change for protruding pavement aggregates count to a variation range for the rate of change for protruding pavement aggregates count.

20. The method according to claim 17, wherein classifying the pavement surface according to a drainage condition type includes comparing the calculated rate of change for the area of protruding pavement aggregates to a variation range for the rate of change for the area of protruding pavement aggregates.

* * * * *